United States Patent
Marino

(10) Patent No.: US 7,600,915 B2
(45) Date of Patent: Oct. 13, 2009

(54) IMAGER BASED OBJECT POSITIONER SYSTEM AND METHOD

(75) Inventor: James F. Marino, La Jolla, CA (US)

(73) Assignee: Trinity Orthopedics, LLC, San Diego, CA (US)

(*) Notice: Subject to any disclaimer, the term of this patent is extended or adjusted under 35 U.S.C. 154(b) by 280 days.

(21) Appl. No.: 11/291,197

(22) Filed: Dec. 1, 2005

(65) Prior Publication Data
US 2006/0115055 A1   Jun. 1, 2006

Related U.S. Application Data

(60) Provisional application No. 60/632,574, filed on Dec. 1, 2004.

(51) Int. Cl.
*A61B 6/04* (2006.01)
*A61B 6/12* (2006.01)

(52) U.S. Cl. .................. 378/204; 378/205; 378/207; 600/426; 600/429

(58) Field of Classification Search ........... 378/195, 378/196, 197, 198, 208, 209, 204, 207, 42, 378/205; 600/426, 429
See application file for complete search history.

(56) References Cited

U.S. PATENT DOCUMENTS

| | | | |
|---|---|---|---|
| 2,232,014 A | | 2/1941 | Simon |
| 2,818,510 A | | 12/1957 | Verse |
| 4,341,279 A | | 7/1982 | Waerve |
| 4,481,656 A | | 11/1984 | Janssen et al. |
| 4,697,661 A | | 10/1987 | Pajerski et al. |
| 4,853,948 A | * | 8/1989 | Huettenrauch et al. ...... 378/177 |
| 5,189,690 A | * | 2/1993 | Samuel ........................ 378/162 |
| 5,283,808 A | * | 2/1994 | Cramer et al. ............... 378/206 |
| 5,386,453 A | | 1/1995 | Harrawood et al. |
| 5,426,687 A | * | 6/1995 | Goodall et al. ............... 378/206 |
| 5,891,034 A | * | 4/1999 | Bucholz ....................... 600/426 |
| 6,095,685 A | | 8/2000 | Tamura |
| 6,131,690 A | | 10/2000 | Galando et al. |
| 6,215,846 B1 | * | 4/2001 | Mazess et al. ................. 378/62 |
| 6,221,082 B1 | | 4/2001 | Marino et al. |
| 6,237,707 B1 | | 5/2001 | Lyke et al. |
| 6,266,394 B1 | | 7/2001 | Marino |
| 6,281,506 B1 | * | 8/2001 | Fujita et al. ............ 250/370.09 |

(Continued)

FOREIGN PATENT DOCUMENTS

WO   WO 00/04839   2/2000

(Continued)

*Primary Examiner*—Allen C. Ho
(74) *Attorney, Agent, or Firm*—Fred C. Hernandez; Mintz, Levin, Cohn, Ferris, Glovsky and Popeo P.C.

(57) ABSTRACT

An apparatus and a method for guiding the placement of an object to a desired location based on an image generated by an image intensifier where the apparatus includes a first coupling mechanism that is configured to be releaseably attachable to one of the transmitter and receiver of the image intensifier and a second coupling mechanism that is coupled to the first coupling mechanism and includes an object holding mechanism, the object holding mechanism is configured to releaseably hold the object and where at least a portion of the second coupling mechanism is visible in the image generated by the image intensifier when the apparatus is attached to the image intensifier.

13 Claims, 18 Drawing Sheets

U.S. PATENT DOCUMENTS

| | | | |
|---|---|---|---|
| 6,285,902 B1 * | 9/2001 | Kienzle et al. | 600/427 |
| 6,374,937 B1 | 4/2002 | Galando et al. | |
| 6,461,039 B1 | 10/2002 | Klotz et al. | |
| 6,466,641 B1 | 10/2002 | Virta et al. | |
| 6,470,207 B1 * | 10/2002 | Simon et al. | 600/426 |
| 6,471,399 B1 * | 10/2002 | Zylka et al. | 378/207 |
| 6,491,429 B1 | 12/2002 | Suhm | |
| 6,519,319 B1 | 2/2003 | Marino et al. | |
| 6,530,930 B1 | 3/2003 | Marino et al. | |
| 6,814,490 B1 | 11/2004 | Suhm et al. | |
| 6,830,375 B2 | 12/2004 | Deshpande | |
| 6,882,700 B2 | 4/2005 | Wang et al. | |
| 6,956,202 B2 * | 10/2005 | Sabczynski et al. | 250/252.1 |
| 6,984,066 B2 * | 1/2006 | Borom | 378/209 |
| 2004/0234039 A1 | 11/2004 | Karaus et al. | |
| 2005/0094770 A1 | 5/2005 | Fadler et al. | |
| 2005/0171420 A1 | 8/2005 | Boese et al. | |
| 2007/0127626 A1 | 6/2007 | Marino | |

FOREIGN PATENT DOCUMENTS

| | | |
|---|---|---|
| WO | WO 00/10461 | 3/2000 |
| WO | WO 00/62687 | 10/2000 |
| WO | WO 01/97680 | 12/2001 |
| WO | WO 2007/062133 | 5/2007 |

* cited by examiner

IMAGER BASED OBJECT POSITIONER SYSTEM AND METHOD

CROSS REFERENCE TO RELATED APPLICATIONS

This invention is related to Provisional Patent Application 60/632,574, filed Dec. 1, 2004, and entitled "Image Intensifier Based Percutaneous Drill Bit, Screw, and Pin Guide", which is hereby incorporated by reference for its teachings.

BACKGROUND

1. Field of the Invention

The invention relates generally to imager related guides, and more particularly, to image intensifier related guides.

2. Description of Related Art

In many procedures including medical related procedures imagers, such as electromagnetic based image intensifiers may be employed to localize or isolate points or planes of interest. The resultant images (generated by the imager(s)) may be used to place one or more objects near or adjacent the point(s) or plane(s) of interest. It is desirable to be able to employ the imager to actively aid in the placement of the object(s). The present invention provides such a system and method.

SUMMARY OF THE INVENTION

The present invention includes an apparatus and a method for guiding the placement of an object to a desired location based on an image generated by an image intensifier. In an embodiment the apparatus includes a first coupling mechanism that is configured to be releaseably attachable to one of the transmitter and receiver of the image intensifier. The apparatus also includes a second coupling mechanism that is coupled to the first coupling mechanism and includes an object holding mechanism. In an embodiment the object holding mechanism is configured to releaseably hold the object and at least a portion of the second coupling mechanism is visible in the image generated by the image intensifier when the apparatus is attached to the image intensifier.

In an embodiment the first coupling mechanism may be substantially not visible in the image generated by the image intensifier when the apparatus is attached to the image intensifier. In addition, the second coupling mechanism may be substantially not visible in the image generated by the image intensifier when the apparatus is attached to the image intensifier except for at least one orientation indication. Further, at least a segment of the object holding mechanism may be visible in the image generated by the image intensifier when the apparatus is attached to the image intensifier.

In an embodiment, image intensifier may have a central axis between the transmitter and receiver and the object holding mechanism may be substantially coaxial with the image intensifier central axis. In addition, the second coupling mechanism may enable the object holding mechanism to moved along the image intensifier central axis. In addition, the second coupling mechanism may enable the object holding mechanism to be moved around the image intensifier central axis. In an embodiment the image intensifier may be a mobile digital fluoroscopy device. Further, the object may be a medical device.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein.

DETAILED DESCRIPTION

Throughout this description, embodiments and variations are described for the purpose of illustrating uses and implementations of the invention. The illustrative description should be understood as presenting examples of the invention, rather than as limiting the scope of the invention.

Figure 1A:
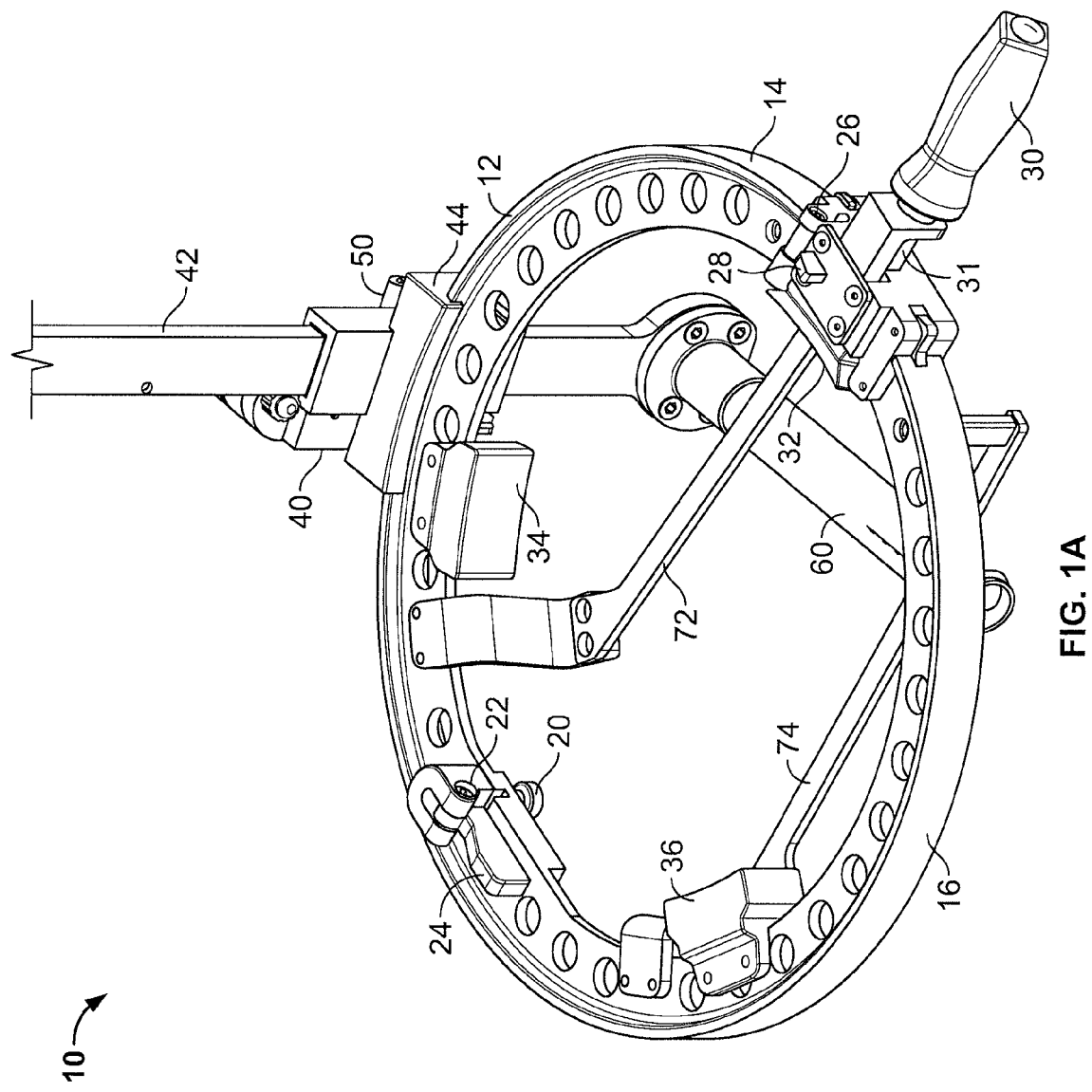
FIG. 1A is an isometric view of an imager based object positioner system in accordance with an embodiment of the present invention.
Figure 1B:
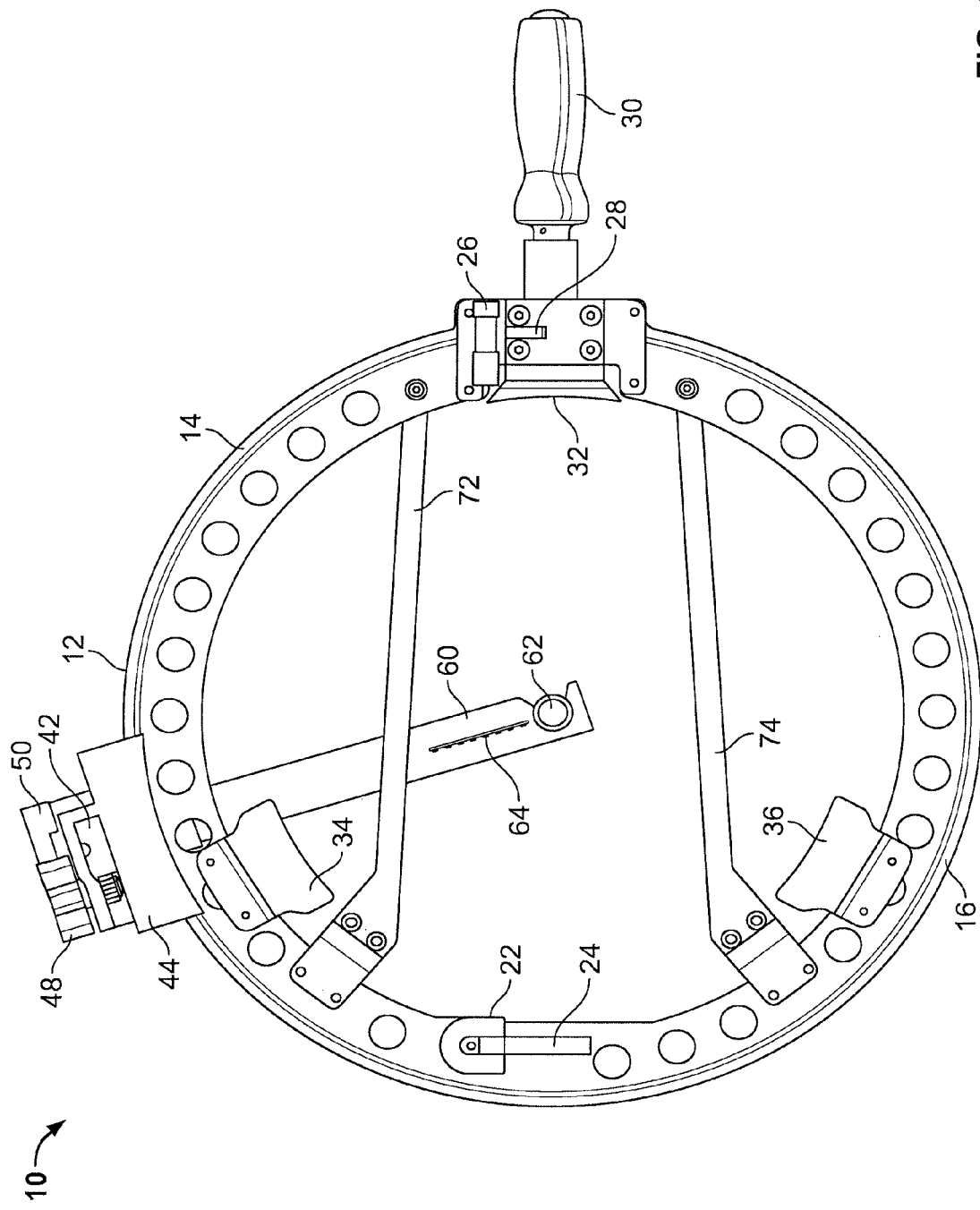
FIG. 1B is a top view of the imager based object positioner system shown in FIG. 1A.
Figure 1C:
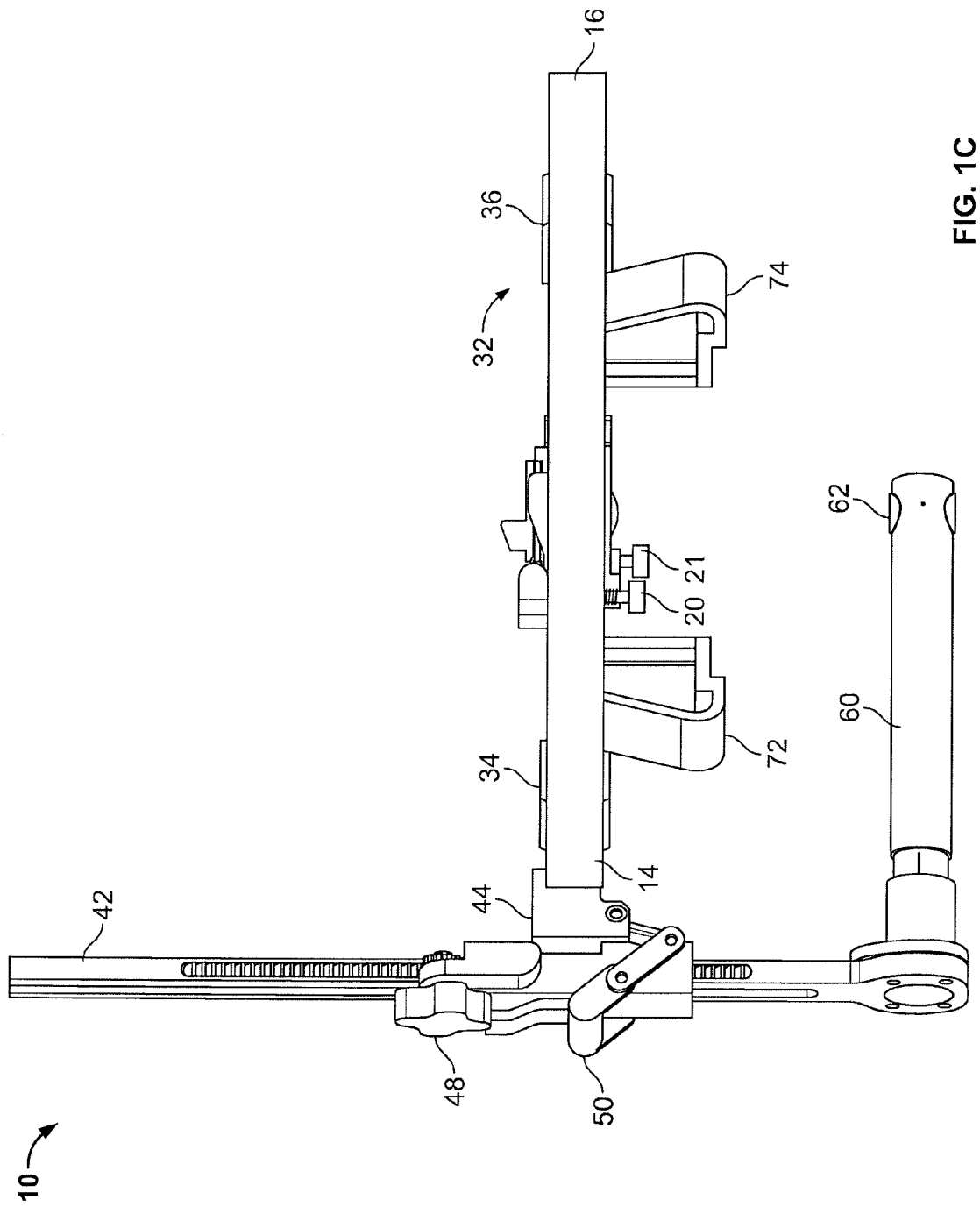
FIG. 1C is a side view of the imager based object positioner system shown in FIG. 1A.

FIG. 1A is an isometric view, FIG. 1B is a top view, and FIG. 1C is a side view of an imager based object positioner system 10 in accordance with an embodiment of the present invention. The imager based object positioner system 10 includes a first rail section 14, a second rail section 16, a moveable clamp 32, immoveable claims 34, 36, a vertical offset mechanism 40, and placement/stabilizer bars 72, 74. In an embodiment the first rail section 14 is coupled to the second rail section 16 via two releasable hinges 22, 26. In an embodiment a handle 30 is coupled to the moveable clamp 32 and screw 31. In an embodiment three clamps 32, 34, 36 may be used to engage a transmitter of an imager. In an embodiment the imager is an imager intensifier system including an image intensifier or receiver supported by a C-ARM in a mobile digital fluoroscope.

In an embodiment the releasable hinge 22 includes a release mechanism 20 and limiter 24 and the releasable hinge 26 includes a release mechanism 21 and limiter 28. The vertical offset mechanism or apparatus 40 includes a releasable car 44, vertically translatable arm 42, car release assembly 50, and guide boom 60. In an embodiment, the car 44 release-ably engages the circular rail 12 formed by the two rail sections 14, 16. The car 44 may be move along the rail 12 when the car release assembly 50 is disengaged in an embodiment. In an embodiment the boom 60 is coupled to a distal end of the arm 42 and includes an object mounting bushing 62.

Figure 2A:
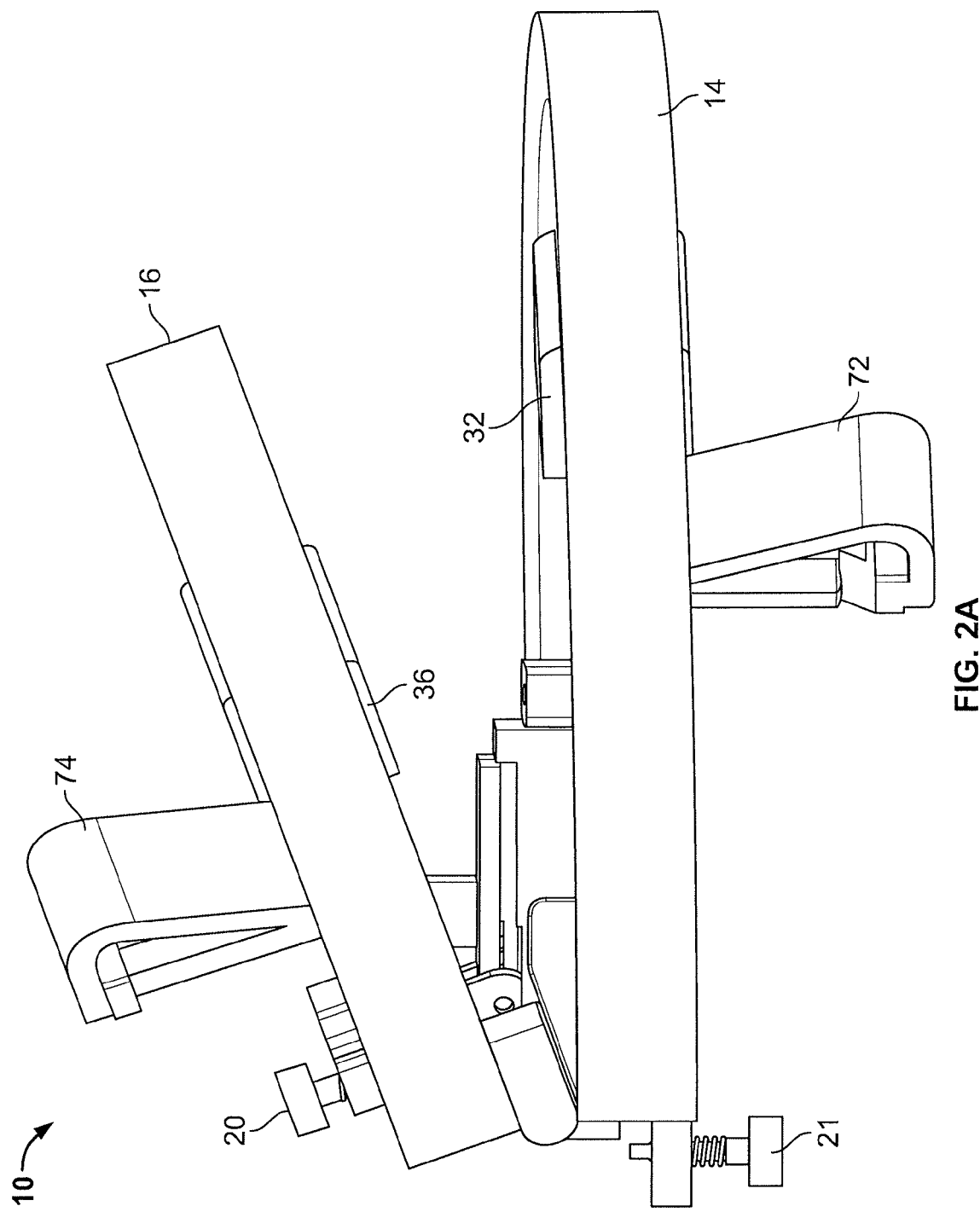
FIG. 2A is a side view of a portion of the imager based object positioner system shown in FIG. 1A in a folded configuration in accordance with another embodiment of the present invention.
Figure 2B:
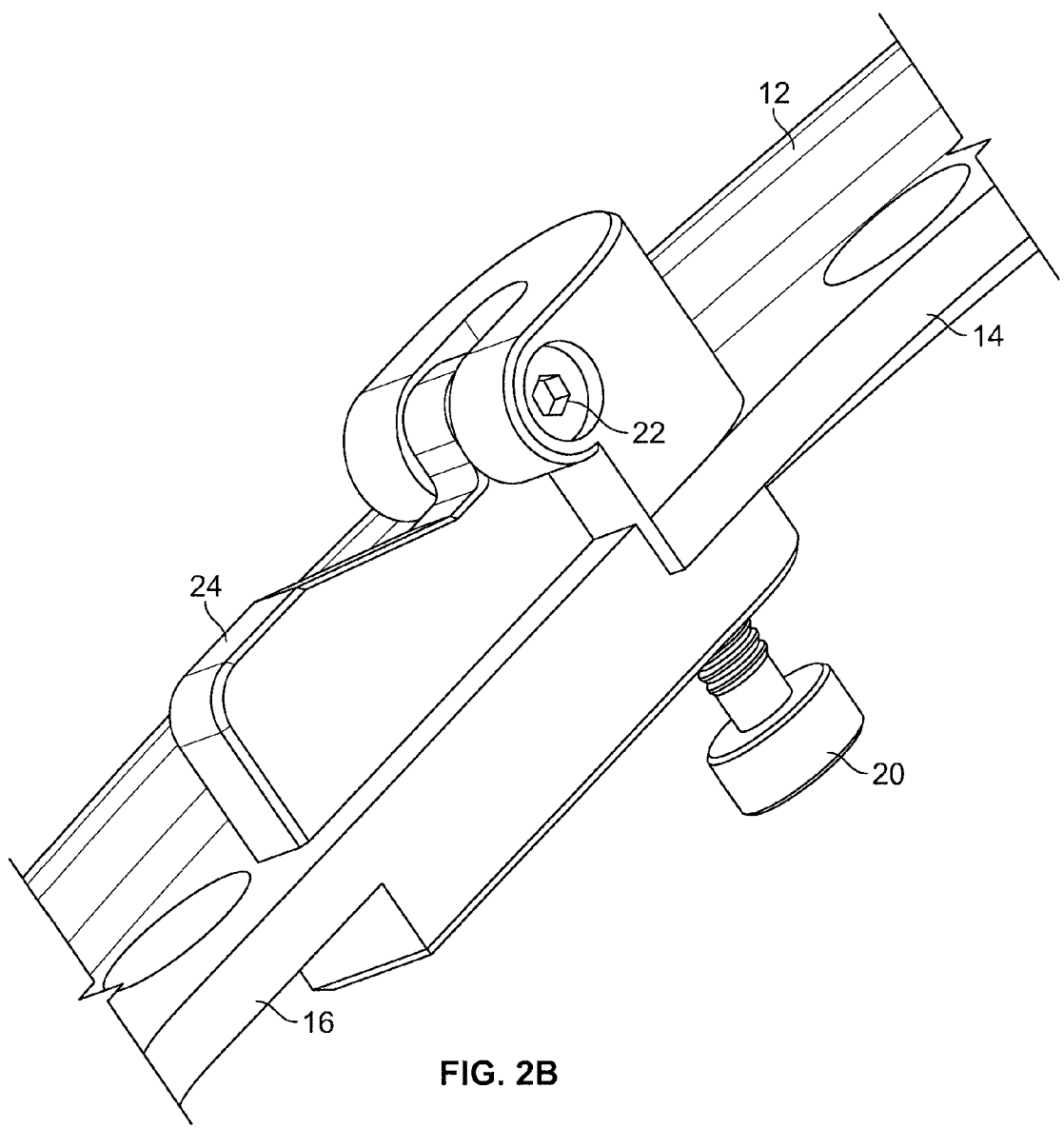
FIG. 2B is an enlarged isometric view of a hinge of the foldable portion of the imager based object positioner system shown in FIG. 2A.

FIG. 2A is a side view of the imager based object positioner system 10 shown in FIG. 1A in a folded configuration without the vertical offset 40 attached in accordance with another embodiment of the present invention. FIG. 2B is an enlarged isometric view of a hinge 22 of the foldable portion of the imager based object positioner system 10 shown in FIG. 2A. In this configuration, the release mechanisms 20, 21 had been deployed to release hinges 22, 26 so the second rail section 16 may be folded over the first rail section 14. The system 10 may be folded to permit placement in a autoclave for sterilization between use in medical applications. In other embodiment the system 10 may not include hinges 22, 26, and thus be foldable.

Figure 3A:
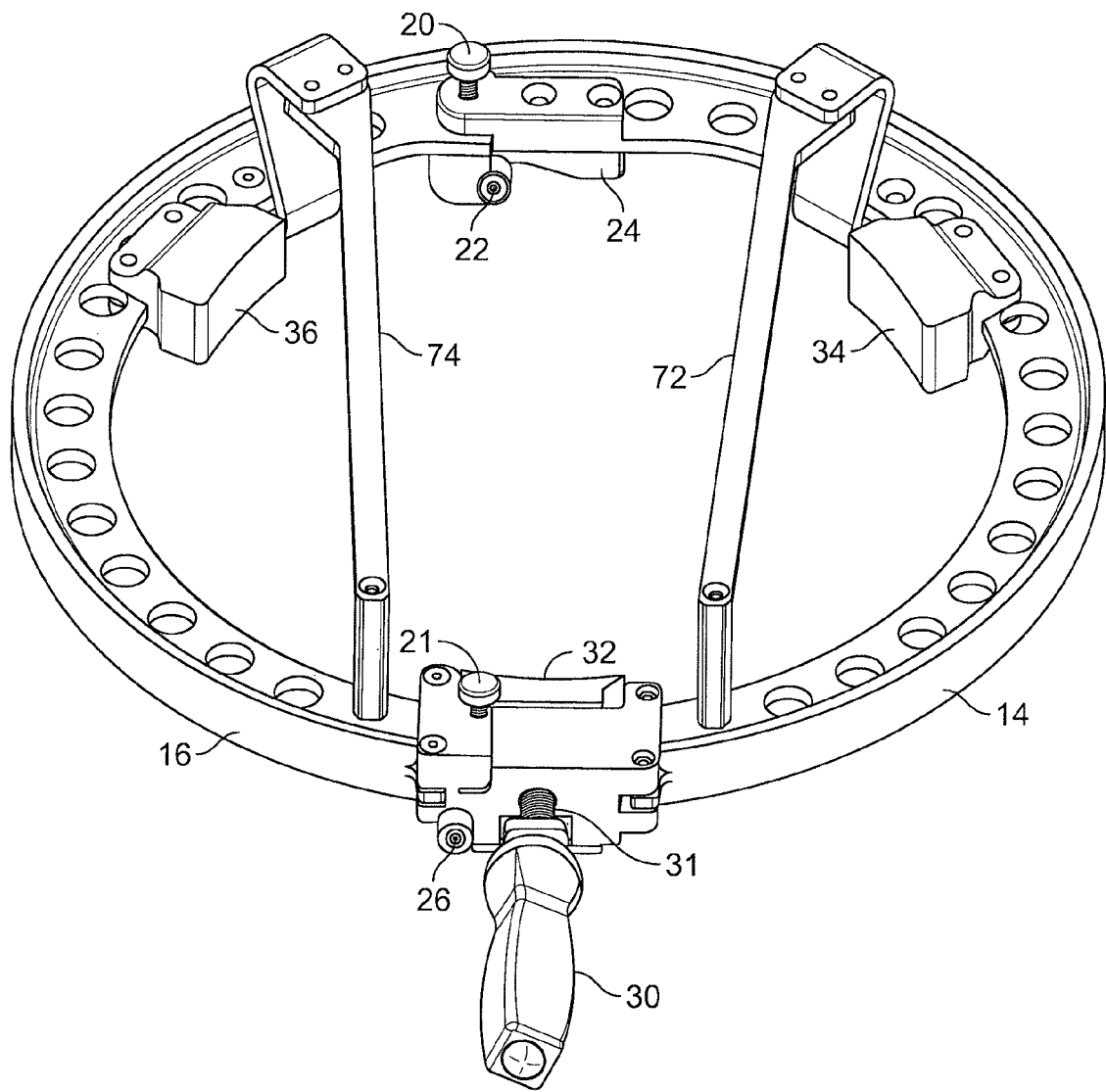
FIG. 3A is a bottom view of the foldable portion of the imager based object positioner system shown in FIG. 2A.
Figure 3B:
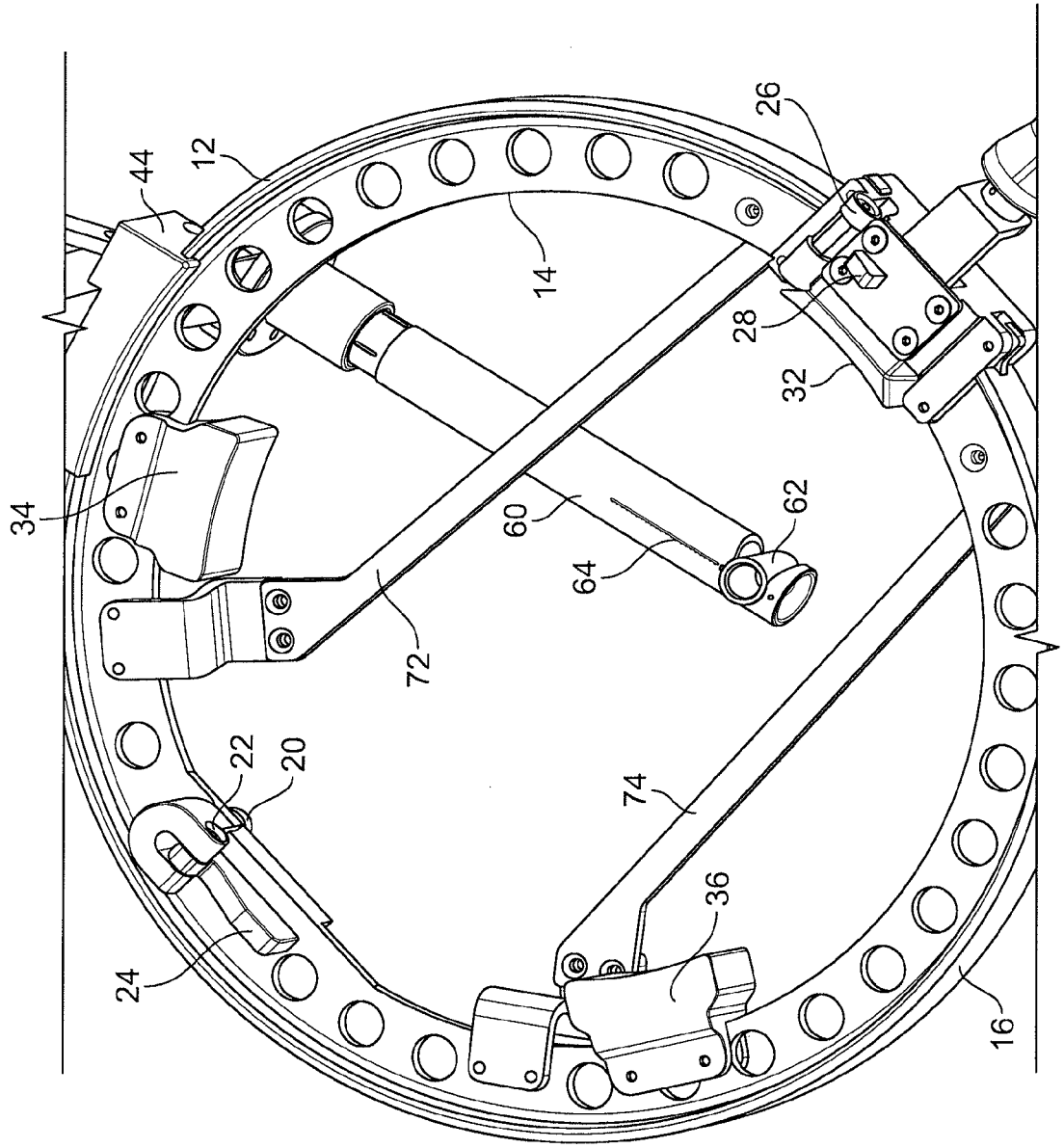
FIG. 3B is a top, partial view of the foldable portion of the imager based object positioner system shown in FIG. 3A.
Figure 3C:
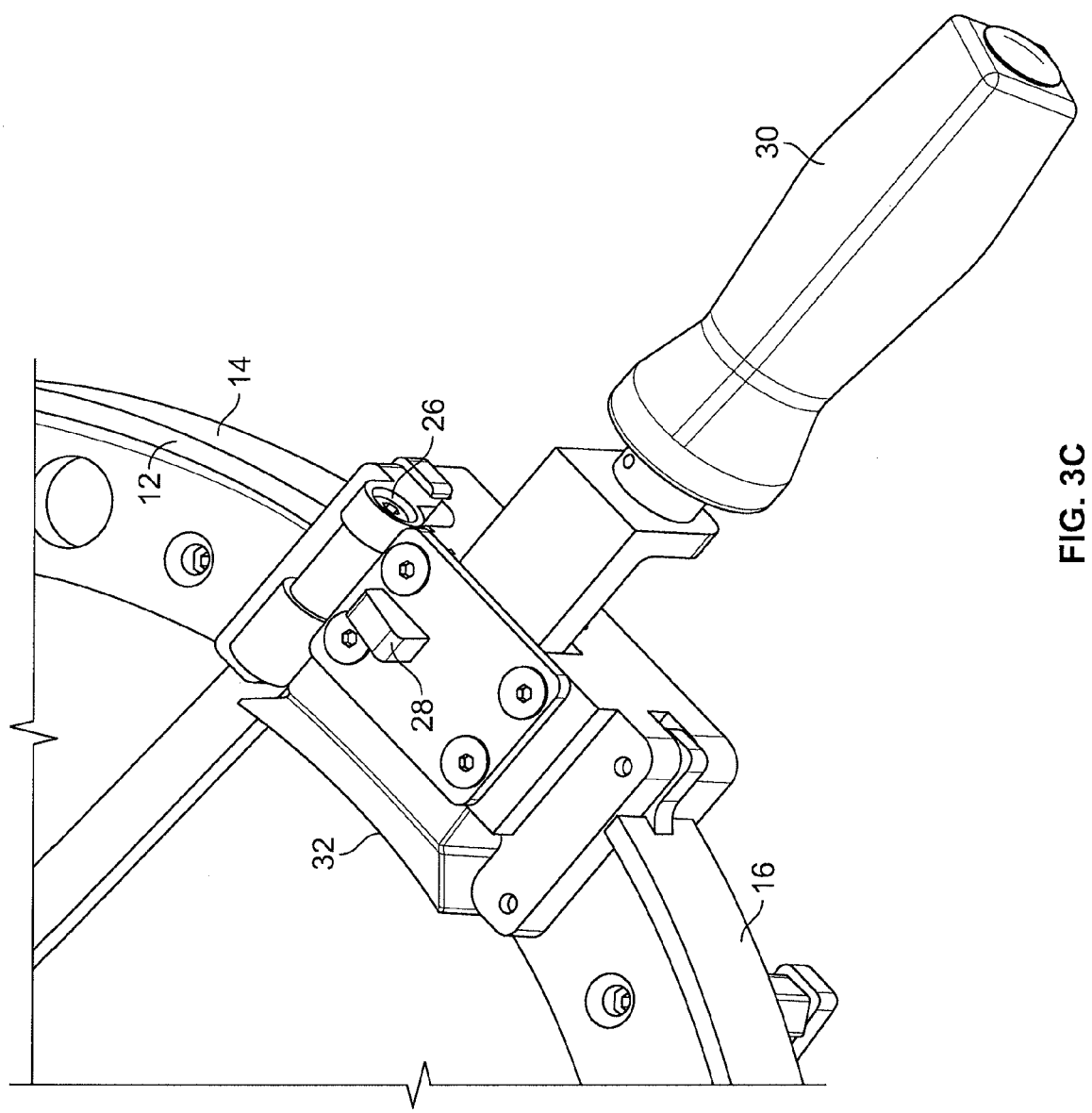
FIG. 3C is a top, partial view of a moveable clamp apparatus of the imager based object positioner system shown in FIG. 3A.

FIG. 3A is a bottom view of the imager based object positioner system 10 shown in FIG. 1A with the vertical offset mechanism 40 removed. FIG. 3B is a top, partial view of the imager based object positioner system 10 shown in FIG. 3A. FIG. 3C is a top, partial view of a moveable clamp mechanism 32 of the imager based object positioner system shown in FIG. 3A. In an embodiment the system 10 may be placed over an imager transmitter and the handle 30 engaged to cause the clamp 32 to apply force in conjunction with clamps 34, 36 against the imager transmitter to release-ably hold the positioner system 10 to the imager transmitter or receiver. In an embodiment the clamps are about 120 degrees apart from adjacent clamps. In an embodiment the handle 30 includes a torque limiter to prevent possible damage to the imager. In another embodiment the position system 10 may include two or more clamps 32, 34, 36 to engage an imager.

Figure 4A:
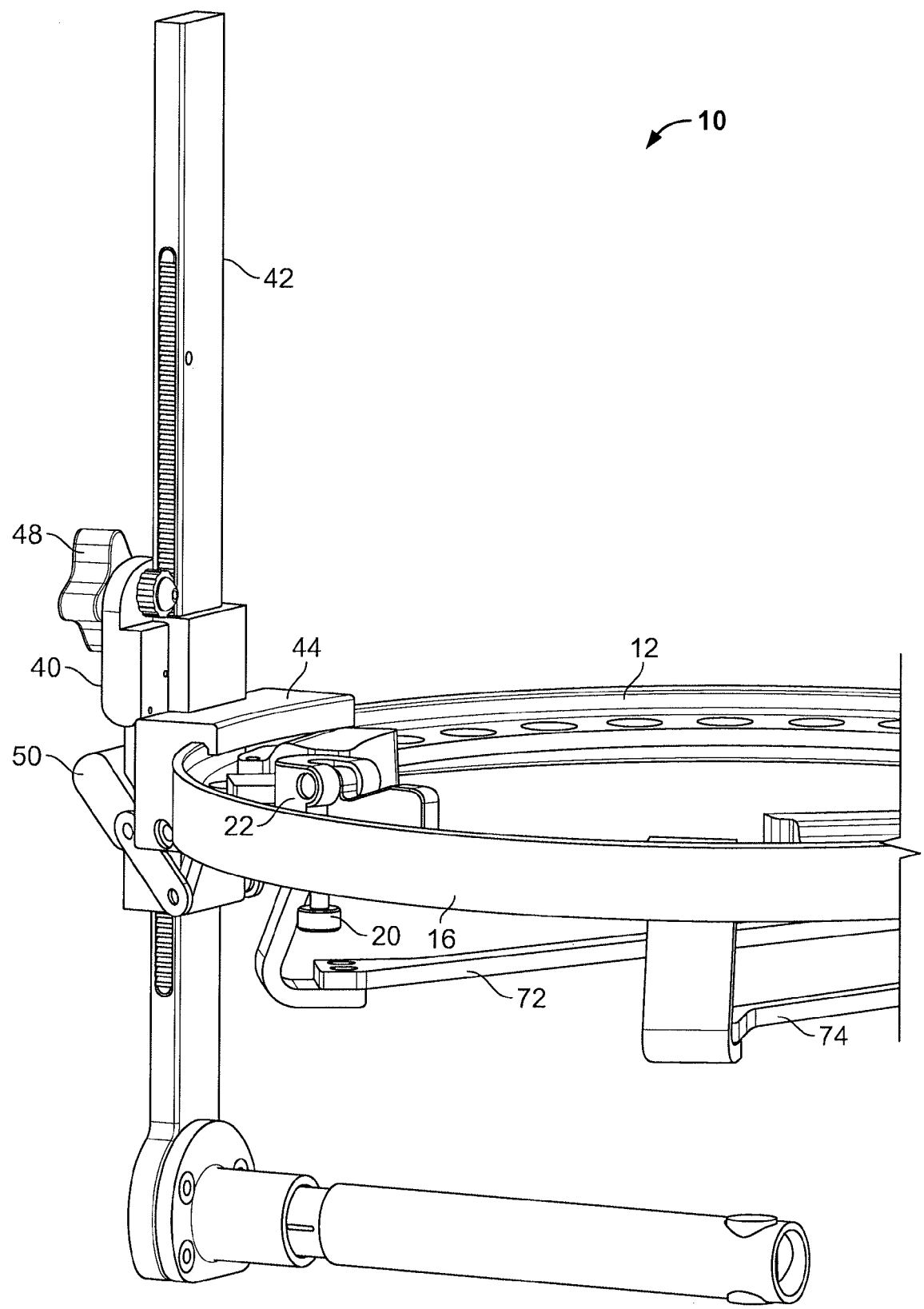
FIG. 4A is a side, partial view of a of the imager based object positioner system shown in FIG. 1A showing an vertical offset system configuration in accordance with another embodiment of the present invention.
Figure 4B:
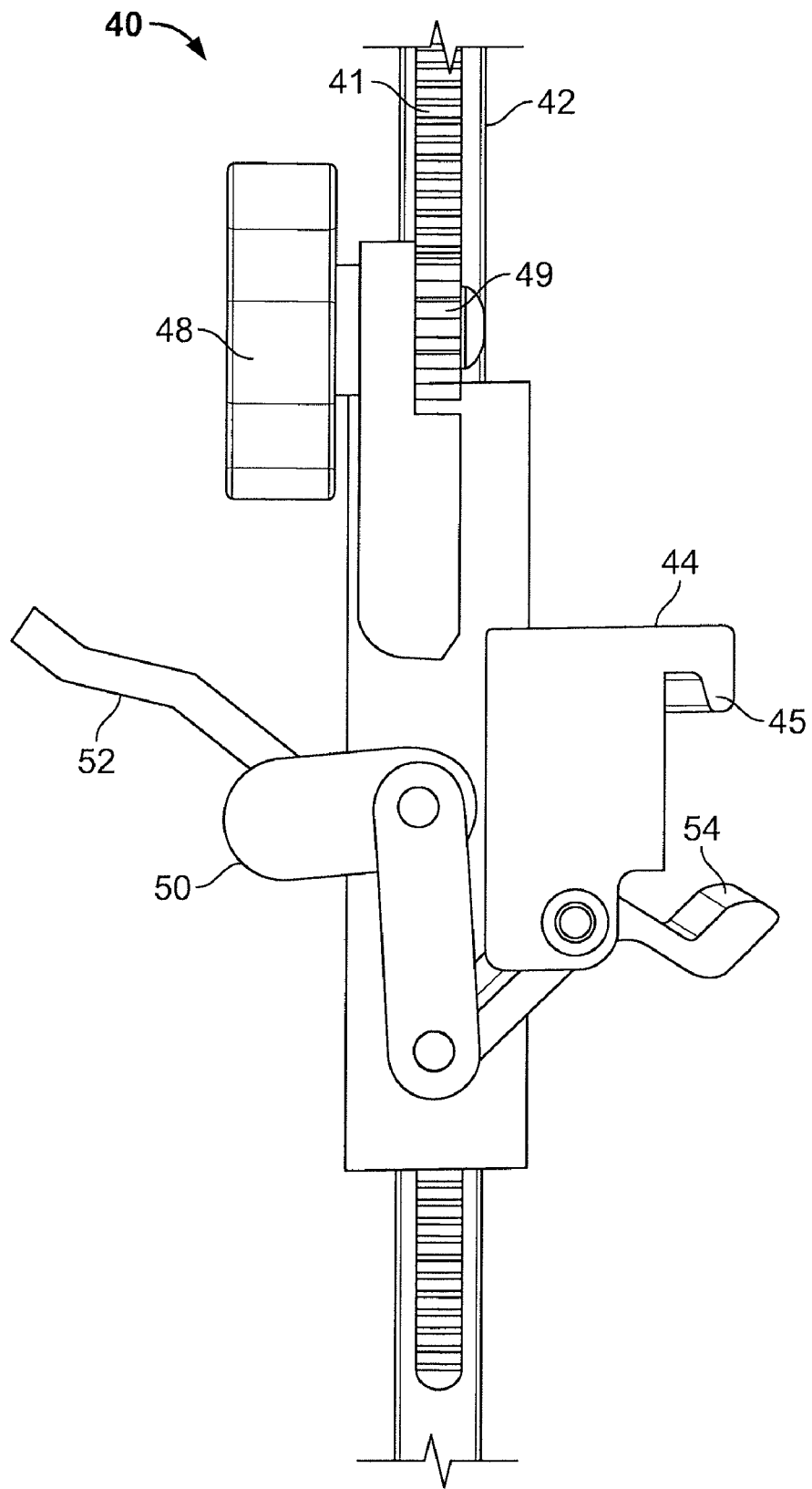
FIG. 4B is a side view of a releasable car system of the vertical offset system shown in FIG. 4A in accordance with another embodiment of the present invention.
Figure 4C:
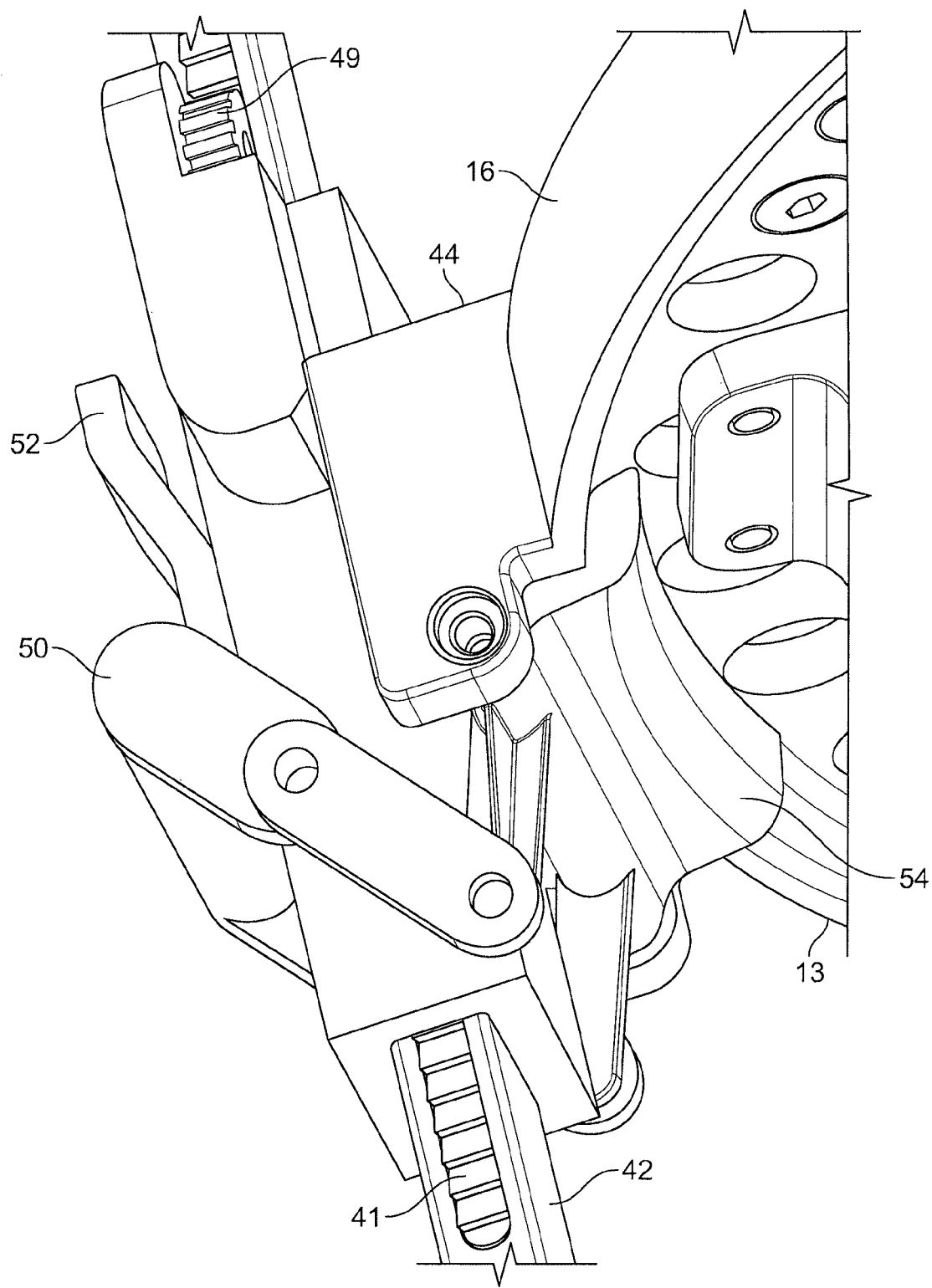
FIG. 4C is an isometric view of the releasable car system of the vertical offset system shown attached to a rail of the foldable section of the imager based object positioner system in accordance with an embodiment of the present invention.

FIG. 4A is a side, partial view of a of the imager based object positioner system 10 shown in FIG. 1A showing an vertical offset system 40 configuration in accordance with another embodiment of the present invention. FIG. 4B is a side view of a releasable car system 44 of the vertical offset system 40 shown in FIG. 4A in accordance with another embodiment of the present invention. FIG. 4C is an isometric view of the releasable car system 44 of the vertical offset system 40 shown attached to a rail 12 of a foldable section 16 of the imager based object positioner system 10 in accordance with an embodiment of the present invention. In an embodiment the car system 44 includes a top rail engagement lip 45, lower track engagement lip 54, car release assembly 50, and release assembly lever 52. In this embodiment the level 52 may be used to release-ably engage the lower rail 13 via the lower track engagement lip 54 and the upper rail 12 via the upper track engagement lip 45.

Figure 4D:
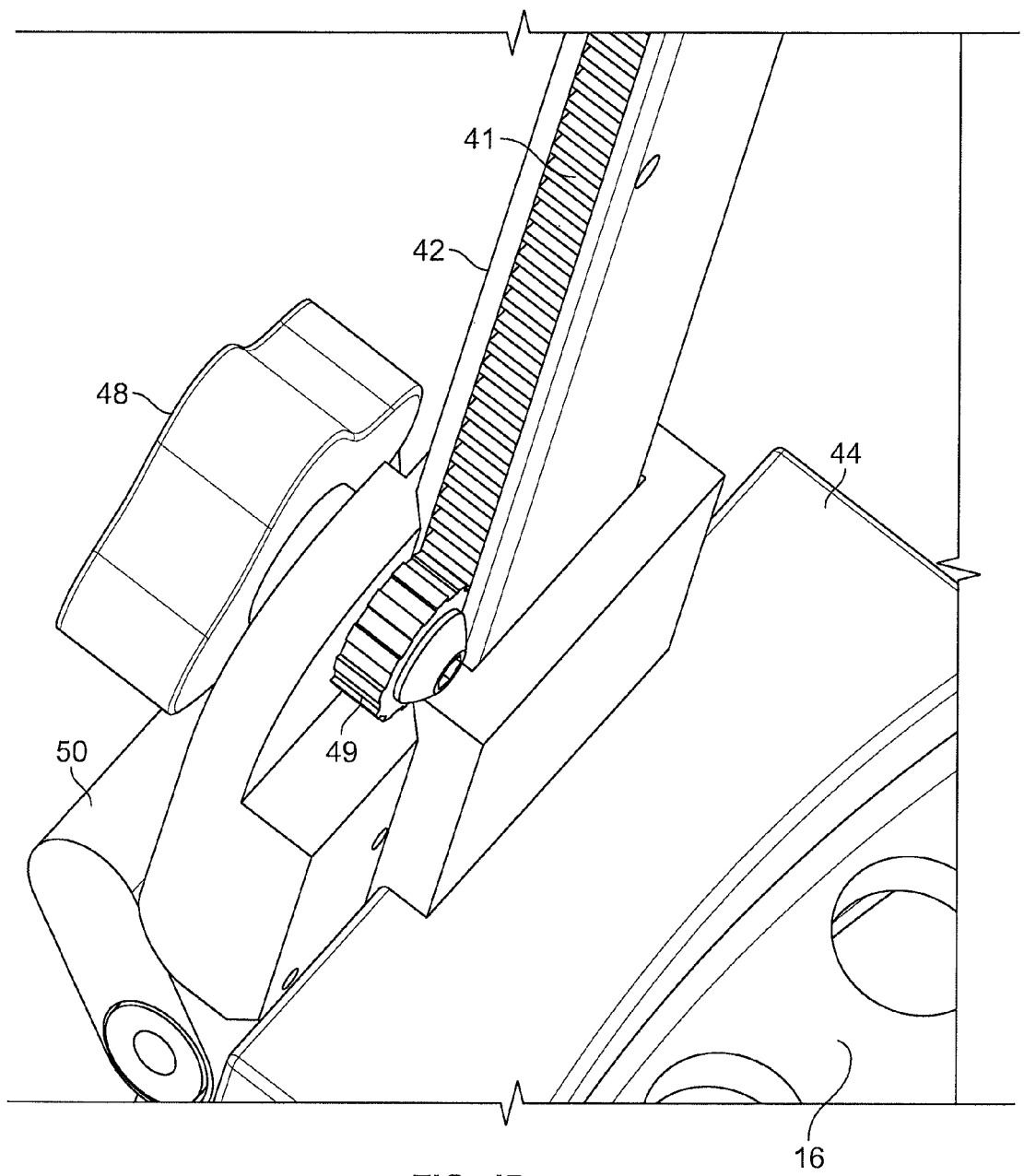
FIG. 4D is an isometric, top view of an vertical level adjustment mechanism of the vertical offset system shown attached to a rail of the foldable section of the imager based object positioner system in accordance with an embodiment of the present invention.
Figure 5A:
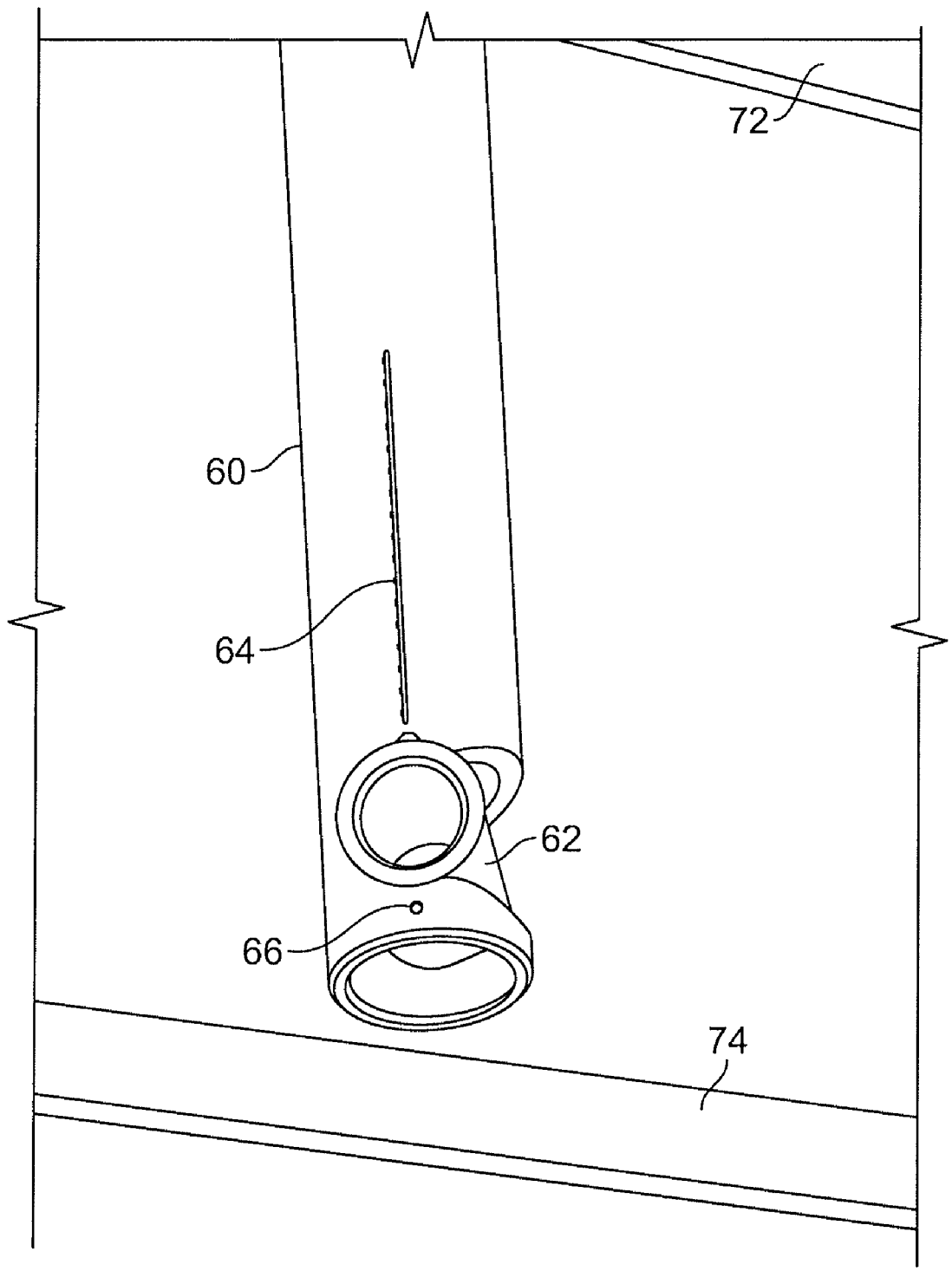
FIG. 5A is a top view of a guide boom of the vertical offset system of the imager based object positioner system shown in FIG. 1A in accordance with an embodiment of the present invention.

FIG. 4D is an isometric, top view of an vertical level adjustment mechanism 48 of the vertical offset system shown attached to a rail 12 of the foldable section 14 of the imager based object positioner system 10 in accordance with an embodiment of the present invention. The adjustment mechanism 48 is coupled to a gear 49. The gear 49 is engaged to the vertical arm 42 via the track 41. FIG. 5A is a top view of a guide boom 60 of the vertical offset system 40 of the imager based object positioner system 10 shown in FIG. 1A in accordance with an embodiment of the present invention. In an embodiment the boom is translucent to the energy generated by the imager to which the system 10 may be attached. In an embodiment the boom may include one or more markers 66, 64 that are opaque to the energy generated by the imager to which the system 10 may be attached. The boom 60 also includes an object coupling bushing 62. In an embodiment bushing 62 may also be opaque to the energy generated by the imager to which the system 10 may be attached.

Figure 5B:
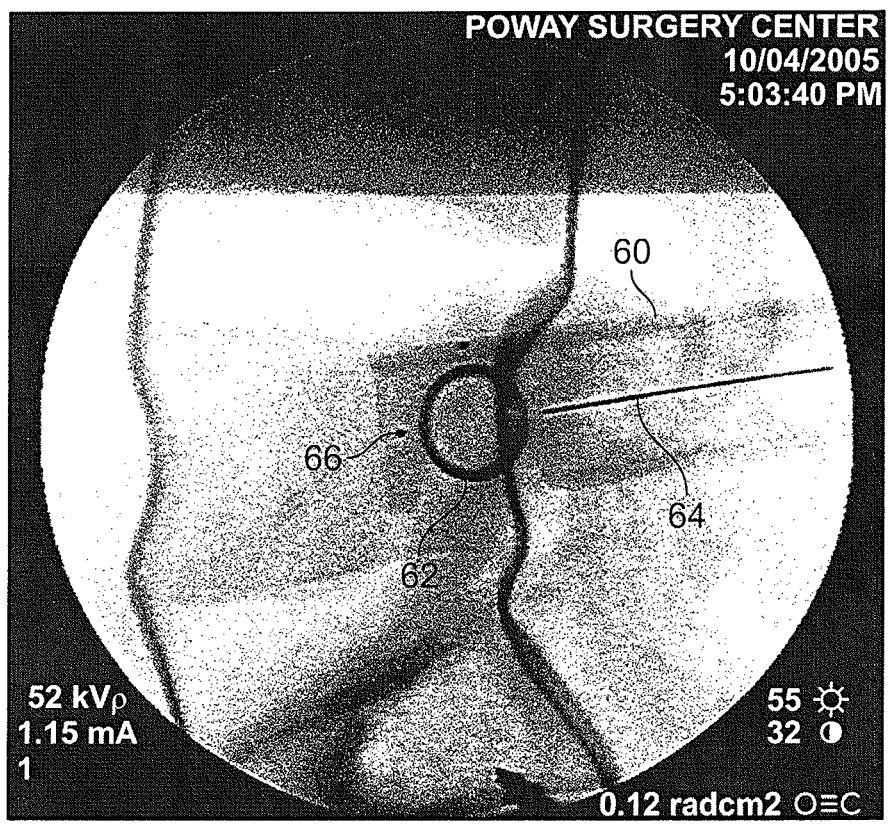
FIG. 5B is a picture of an image generated by an imager of the boom shown in FIG. 5A adjacent to bony anatomy in accordance with an embodiment of the present invention.
Figure 5C:
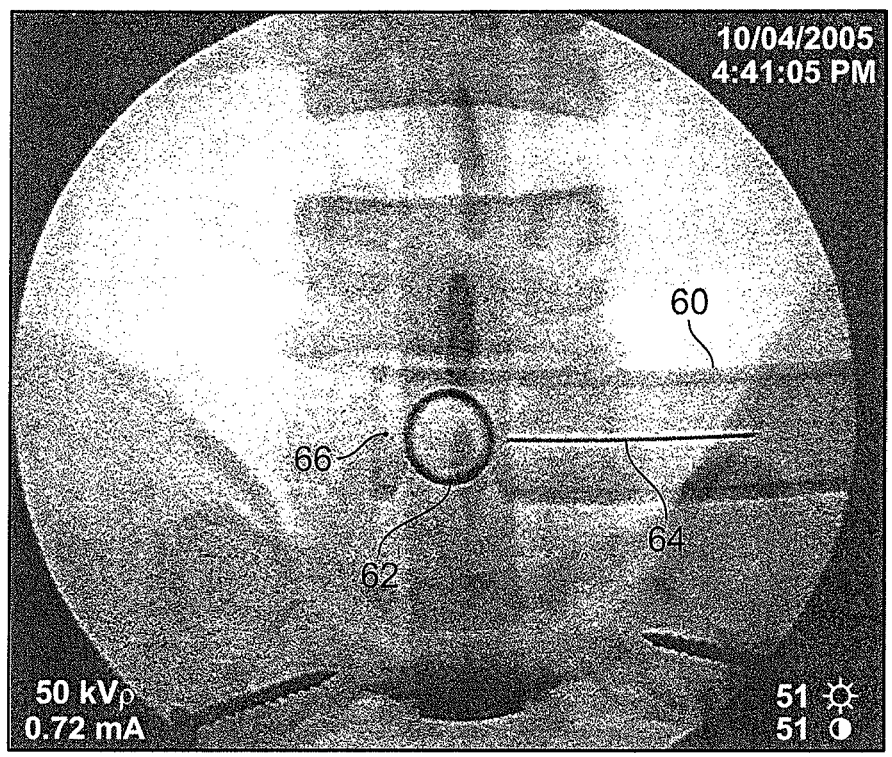
FIG. 5C is a picture of another image generated by an imager of the boom shown in FIG. 5A adjacent to bony anatomy in accordance with an embodiment of the present invention.

FIGS. 5B and 5C are pictures of images generated by an imager including the boom shown in FIG. 5A adjacent to bony anatomy in accordance with an embodiment of the present invention. As shown in these FIGURES the marks 64, 66 and bushing 62 absorb energy generated by an imager enabling their identification in images generated by the imager. The markers 62, 64, 66 may be used to align the bushing with a desired line or plane of approach to desired target. An object may be coupled to the bushing 62 to enable precise placement of the object along the desired line or plane established by the imager while the system 10 remains coupled to the imager.

Figure 6:
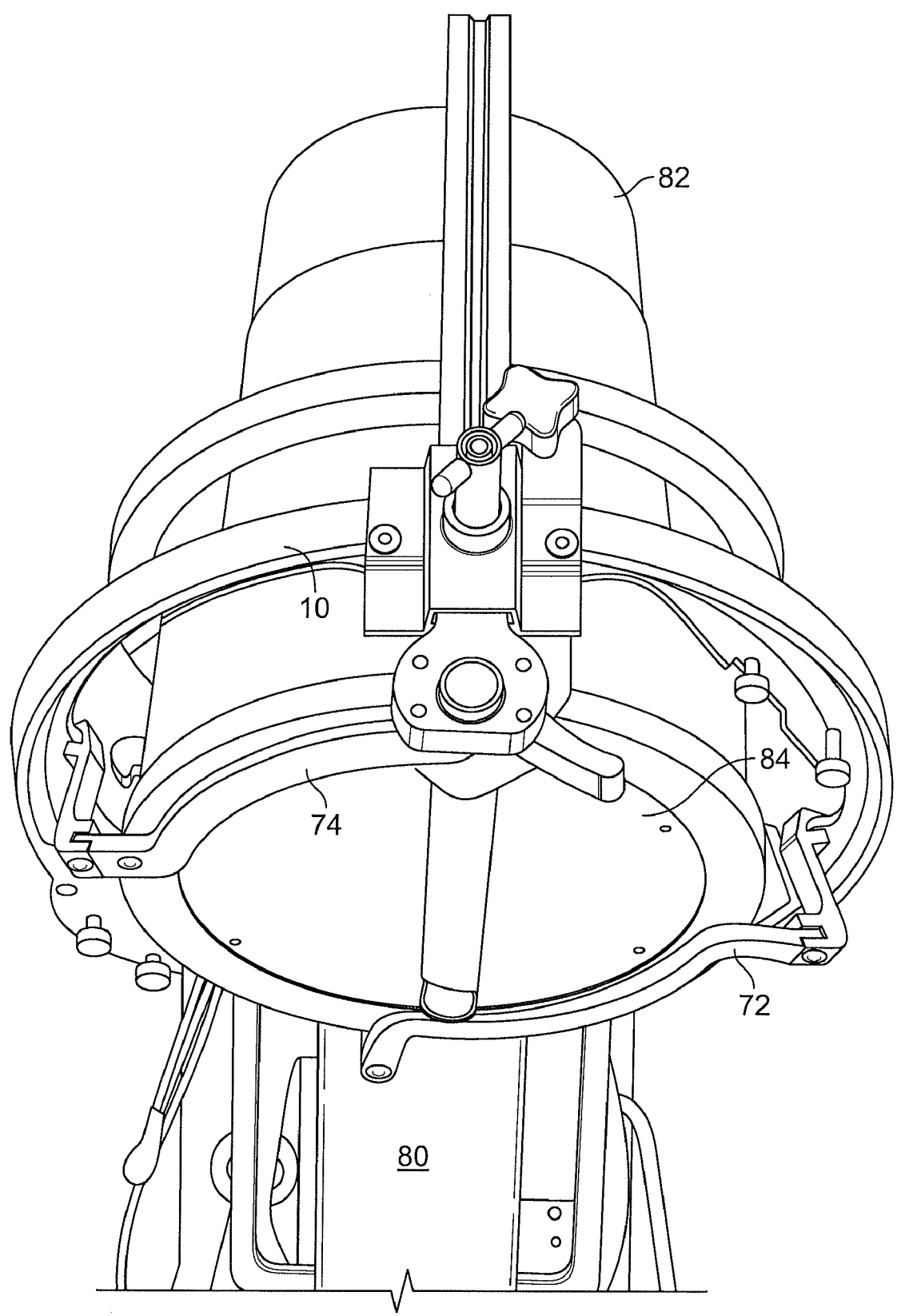
FIG. 6 is a picture of an imager based object positioner system shown in FIG. 1A in accordance with an embodiment of the present invention mounted on an imager.

FIG. 6 is a picture of an imager based object positioner system 10 shown in FIG. 1A in accordance with an embodiment of the present invention mounted on an imager 80. The imager 80 includes a transmitter 82 with a distal end 84, wherein the transmitter 82 is supported by a mechanical linkage suck as a "C-ARM". In this example the imager 80 is a mobile digital fluoroscope. In this embodiment the positioner system 10 is coupled to the transmitter's 82 distal end 84. As also shown in FIG. 6 the placement bar/stabilizer bars 72, 74 engage the imager 80 transmitter's 82 distal end 84 while not blocking energy transmission. In this embodiment the system 10 includes three clamps 32, 34, 36 that, in combination with the stabilization bars 72, 74 securely holds the positioner system 10 to the imager 80 transmitter 82. As shown in FIGS. 5B and 5C and may be seen in FIG. 6, in an embodiment only the boom 60 is positioned in imager's energy field preventing distortion or artifacts in the image generated by an imager coupled to the system 10.

Figure 7A:
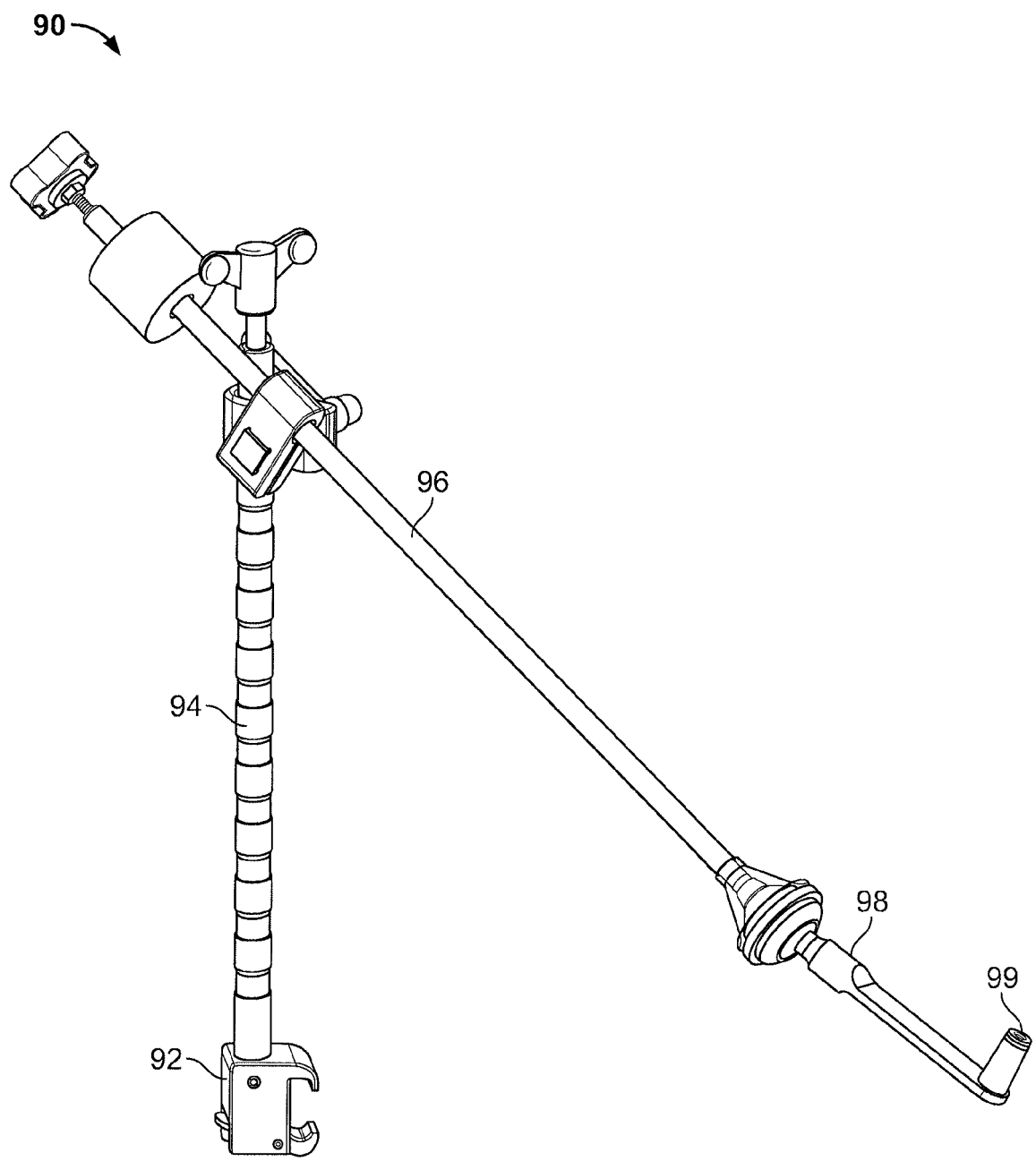
FIG. 7A is a picture of a spatial positioner that may be used in conjunction with the imager based object positioner system shown in FIG. 1A in accordance with an embodiment of the present invention.
Figure 7B:
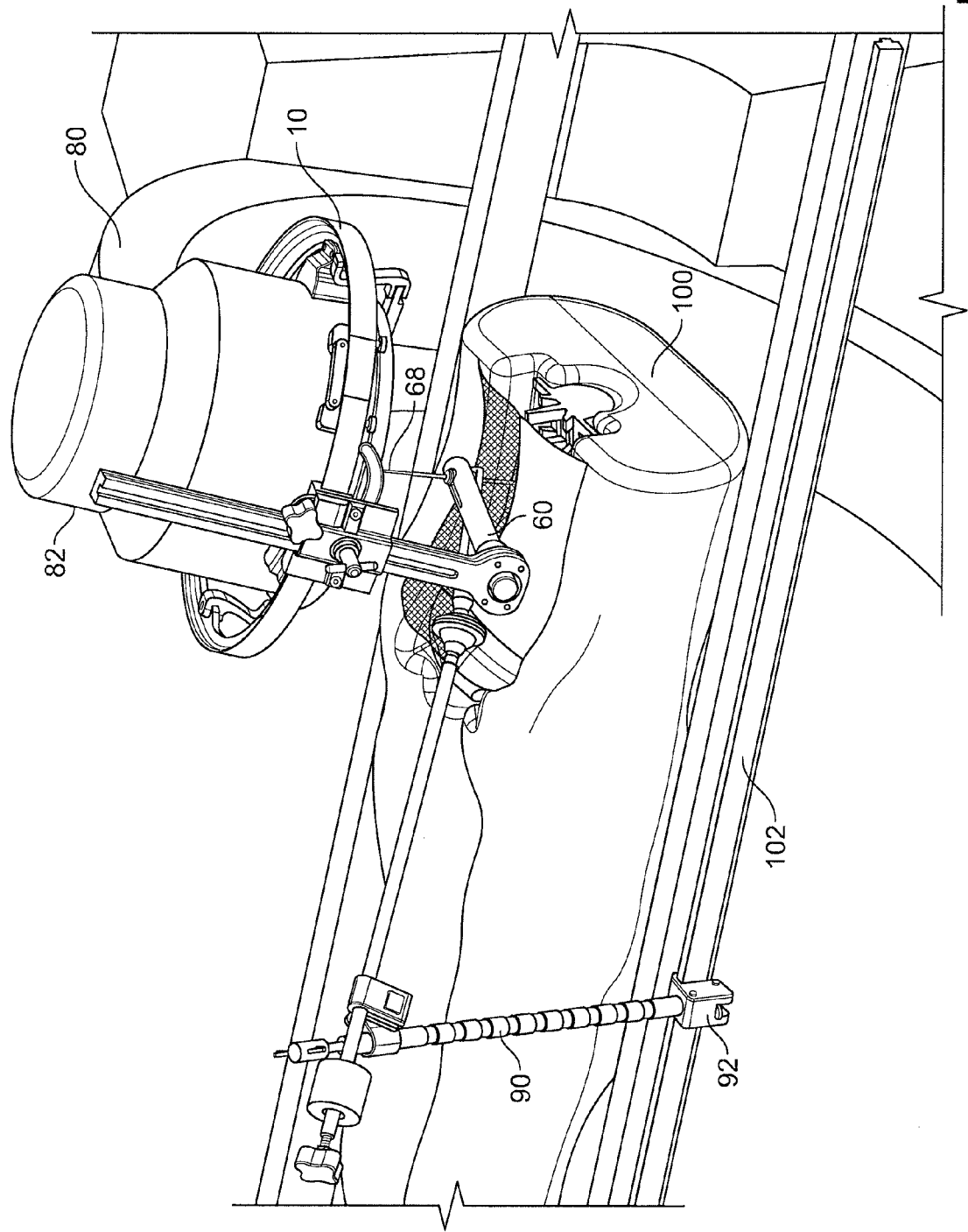
FIG. 7B is a diagram of an imager based object positioner system mounted on an imager and coupled to the spatial positioner shown in FIG. 7A in accordance with an embodiment of the present invention adjacent to exemplary anatomy.
Figure 7C:
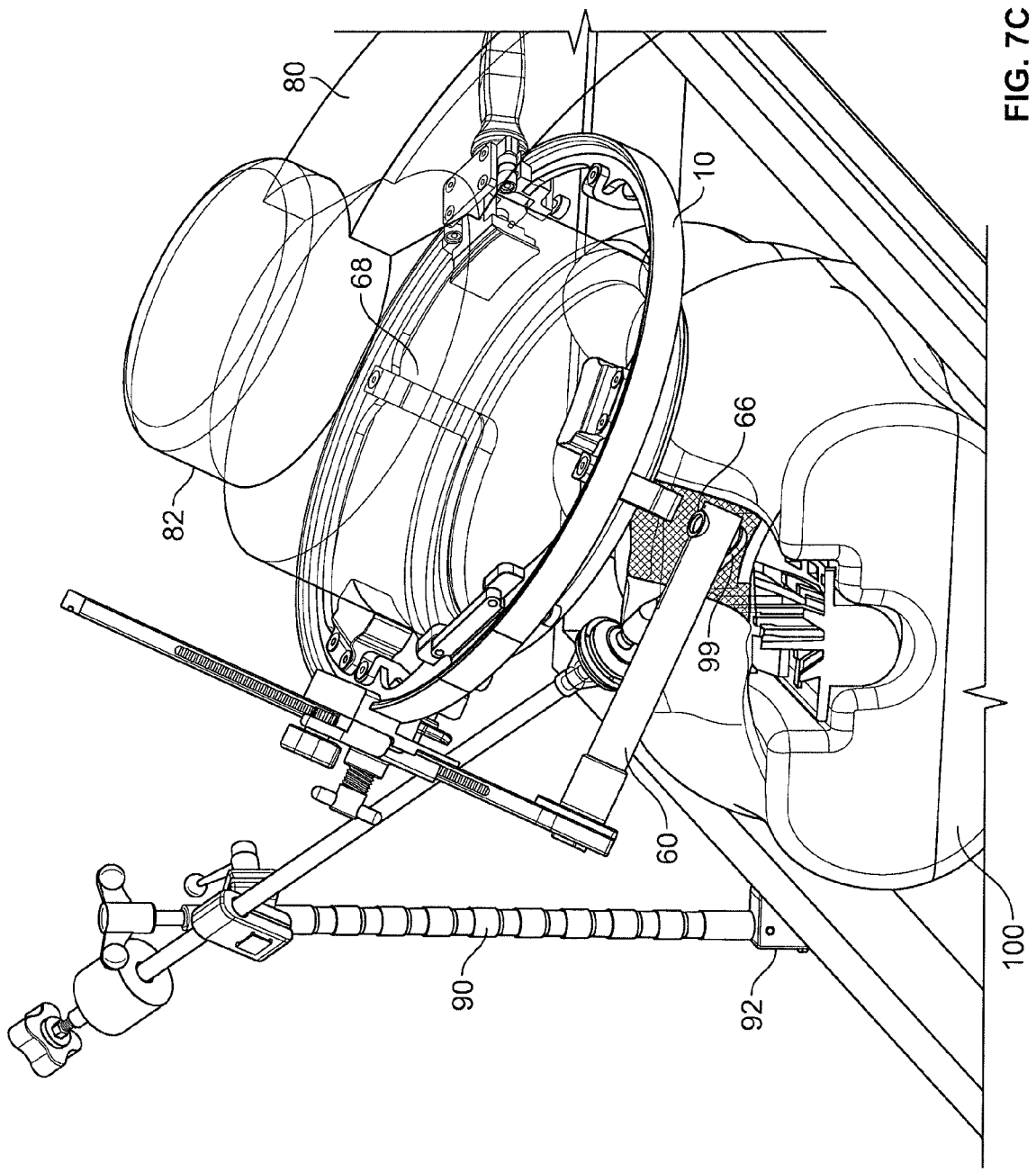
FIG. 7C is another diagram of an imager based object positioner system mounted on an imager and coupled to the spatial positioner shown in accordance with an embodiment of the present invention adjacent to exemplary anatomy.

FIG. 7A is a picture of a spatial positioner 90 that may be used in conjunction with the imager based object positioner system shown 10 in FIG. 1A in accordance with an embodiment of the present invention. The spatial positioner 90 includes a table clamp 92, lockable snake 94, extension arm 96, lockable pivotable tip 98, and bushing engaging member 99. FIG. 7B is a diagram of an embodiment of the imager based object positioner system 10 mounted on an imager and coupled to the spatial positioner shown in FIG. 7A in accordance with an embodiment of the present invention adjacent to exemplary anatomy. In this embodiment, the boom's 60 bushing 62 may be aligned to an anatomical plane or point of anatomy 100 via the imager 80. The spatial positioner's 90 bushing engager 99 is then coupled to the boom's 60 bushing 62. In this embodiment the spatial positioner 90 is coupled to the table 102 via the table clamp 92. In addition, a guide wire 68 is inserted into the anatomy 100 via the boom's 60 bushing 62. The imager 80 may be employed to generate an image to verify proper placement of the guide wire 68 in an embodiment. FIG. 7C is another diagram of an imager based object positioner system mounted on an imager and coupled to the spatial positioner shown in accordance with an embodiment of the present invention adjacent to exemplary anatomy.

In an embodiment the imager 80 and positioner system 10 attached thereto may be removed from the operative field of view leaving the spatial positioner 90. The spatial positioner bushing 99 may have been aligned with a desired target plane or line enabling a user to employ a tool such as the guide wire 68 along the target plane or line. In another embodiment the position system's 10 arm 42 may be extended via the adjustment mechanism 48. In this embodiment the boom's 60 bushing may be used to employ an object or tool along a desired target plane or line where the tool or object may be a medical tool or other tool in non-medical applications. The tools may include a guide wire 68, cannula, obturator, drill, reamer, or endoscope. It is also noted that lever 52 may be released partially so the car 44 may be rotated along the track 12 to move the vertical offset mechanism 40 out of the field of view. In an embodiment the boom 60 bushing 62 remains co-axial with the central axis of the imager 80 as the car 44 is rotated around the track due to the geometry of the rail 12 and bushing 62 distance from the arm 42.

While this invention has been described in terms of a best mode for achieving the objectives of the invention, it will be appreciated by those skilled in the art that variations may be accomplished in view of these teachings without deviating from the spirit or scope of the present invention. For example the positioner system 10 may be used in conjunction with an imager to access an archeological artifact or access a complex mechanical or electrical device.

What is claimed is:

1. A device to assist in the alignment of a visualized axis of an image field of an X-ray machine with an object, comprising:
   a frame comprising an annular rail that attaches to a portion of the X-ray machine such that the annular rail is adapted to encircle a transmitter or receiver of the X-ray machine and such that the frame is positioned adjacent to the perimeter of the image field when the frame is attached to the X-ray machine;
   a boom support arm attached to the frame and extending vertically from the frame;
   a boom attached to the support arm such that a portion of the boom extends into the image field of the X-ray machine when the device is attached to the X-ray machine; and
   at least one radio-opaque marker positioned on the boom such that the radio-opaque marker is in the image field when the device is attached to the X-ray machine.

2. A device as in claim 1, further comprising a bushing on the boom, wherein the boom supports the bushing in a position such that an aperture in the bushing is aligned with the visualization axis.

3. A device as in claim 2, wherein the support arm rotates along the annular rail to a variety of locations from which the boom extends into the image field and wherein a bushing aperture on the boom remains in a position that is aligned with the visualization axis while the support arm rotates.

4. A device as in claim 1, wherein the annular rail includes a clamp system including three pads that engage the X-ray machine to support the rail on the X-ray machine, wherein each pad is positioned on the rail 120 degrees apart from an adjacent pad.

5. A device as in claim 4, wherein the clamp system includes a single securing mechanism that advances only one of the pads toward the X-ray machine to cause the three pads to clamp onto the X-ray machine.

6. A device as in claim 5, wherein the securing mechanism includes a torque limiter mechanism that limits torque applied and thus the compressive load to the X-ray machine so as to prevent damage to the X-ray machine.

7. A device as in claim 1, wherein the frame folds to a size that permits placement of the frame in an autoclave.

8. A device as in claim 1, wherein the boom is at least partially radiolucent.

9. A device as in claim 1, further comprising a vertical offset mechanism coupled to the support arm or the frame, wherein the vertical offset mechanism can be adjusted to vary the amount of vertical offset between the boom and the frame.

10. A device as in claim 1, wherein the boom support arm detaches from the frame to permit the boom to be removed from the image field of the X-ray machine.

11. A device as in claim 1, further comprising a spatial positioner comprising:
    a clamp that attaches to a surgical table;
    a stanchion extending vertically from the clamp;
    an engager arm;
    a first joint that couples the engager arm to the stanchion and that permits variation in the orientation of the engager arm relative to the stanchion;
    a bushing engager that engages a bushing on the boom;
    a second joint that couples the bushing engager to the engager arm;
    wherein the first and second joint permit the bushing engager to be moved to a lockable position wherein the bushing engager is engaged with the bushing.

12. A device as in claim 1, in which the visualized axis within the image field is coaxial with the central image beam of the x-ray machine, such that the effects of beam divergence is absent or negligible.

13. A device as in claim 1, in which the boom can be rotated on the boom support to a position outside of the image field as well as rotated back to a mechanically defined and aligned position within the field.

* * * * *

UNITED STATES PATENT AND TRADEMARK OFFICE
CERTIFICATE OF CORRECTION

| | | |
|---|---|---|
| PATENT NO. | : 7,600,915 B2 | Page 1 of 1 |
| APPLICATION NO. | : 11/291197 | |
| DATED | : October 13, 2009 | |
| INVENTOR(S) | : James F. Marino | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 469 days.

Signed and Sealed this

Fifth Day of October, 2010

David J. Kappos
*Director of the United States Patent and Trademark Office*